United States Patent [19]
Senn et al.

[11] Patent Number: 6,068,474
[45] Date of Patent: May 30, 2000

[54] LIGHT CURING DEVICE

[75] Inventors: Bruno Senn, Buchs; Gregor Fritsche; Gottfried Rohner, both of Altstätten, all of Switzerland

[73] Assignee: Ivoclar AG, Schaan, Liechtenstein

[21] Appl. No.: 09/236,876

[22] Filed: Jan. 26, 1999

Related U.S. Application Data

[60] Provisional application No. 60/085,486, May 14, 1998.

[30] Foreign Application Priority Data

Jan. 30, 1998 [DE] Germany ............ 198 03 755

[51] Int. Cl.⁷ .................................. A61C 1/00
[52] U.S. Cl. ............................ 433/29; 250/504 H
[58] Field of Search ................ 433/29, 229; 250/504 H

[56] References Cited

U.S. PATENT DOCUMENTS

| | | | |
|---|---|---|---|
| 4,298,806 | 11/1981 | Herold | 250/504 H |
| 5,471,129 | 11/1995 | Mann | 433/141 |
| 5,803,729 | 9/1998 | Tsimerman | 433/29 |
| 5,820,829 | 10/1998 | Schodel | 422/133 |
| 5,879,159 | 3/1999 | Cipolla | 433/29 |

FOREIGN PATENT DOCUMENTS

| | | |
|---|---|---|
| 391 263 | 9/1990 | Austria . |
| 0753287 | 1/1996 | European Pat. Off. . |
| 2901534 | 7/1979 | Germany . |
| 2841112 | 4/1980 | Germany . |
| 3820413 | 11/1989 | Germany . |
| 3840984 | 6/1990 | Germany . |
| 4211230 | 4/1992 | Germany . |
| 9017070 | 5/1992 | Germany . |

*Primary Examiner*—John J. Wilson
*Attorney, Agent, or Firm*—John C. Thompson; Alan S. Korman

[57] ABSTRACT

In a light curing device which is especially suitable for light-induced polymerization of dental material in the mouth of a patient, a light source is provided which is housed together with a reflector in the hand-held device together with a cooling fan. The reflector reflects the radiation emitted by the light source. The light source is supported within a substantially dust-tight light source casing having cooling ribs provided at its exterior.

18 Claims, 2 Drawing Sheets

LIGHT CURING DEVICE

This application claims benefit of provisional application Ser. No. 60/085,486 filed May 14, 1998.

BACKGROUND OF THE INVENTION

The invention relates to a light curing device, especially for a light-induced polymerization of the dental materials in the mouth of a patient, wherein the light curing device comprises a light source that is received in the hand-held portion together with a reflector for the light emitted by the light source and also comprises a cooling fan. The light source is supported in a substantially dust-tight light source casing and has provided at its exterior cooling ribs. The light source casing is of a two-part construction and has a counter cone member facing the light source.

Such a light curing device is known from German Offenlegungsschrift 29 01 534. In this known light curing device a reflector is embodied as a thin layer filter and is designed to reflect the light emitted by the light source and required for polymerization. Light of longer wave length, however, is to penetrate the reflector. The penetrating infrared radiation is then to be absorbed by a heat conducting element arranged in an air flow and is to be dissipated in this manner. In addition, cooling air flows along the holder for the reflector and thus also contributes to the cooling of the reflector. An absorption filter is provided on the light guide and is designed to absorb heat radiation present thereat.

Furthermore, it is already known to use instead of the holder a counter cone member which additionally reflects the light reflected by the reflector and thus contributes to improved light output. A light curing device with such a counter cone member, is for example, known from German Offenlegungsschrift 42 11 230.

Light curing devices employed in the dental practice must have a high light output and must provide this light output reliably within a precisely defined time interval. The dentist must be able to rely on the device in regard to complete polymerization being achieved by the dispensed amount of radiation. Otherwise, the filling would be soft and gaps could form at the edges which would result in secondary tooth decay which may result in liability suits being filed against the dentist in regard to insufficient curing and the thus caused problems.

It is therefore especially important that even after extended operation of the light curing device a sufficient light output is realized.

In order to ensure this, a certain reserve potential is employed with respect to the light output so that the operational voltage can be slightly increased when the optimum efficiency of the light source is reduced. Even though light sources of a very high light efficiency, especially in the form of halogen lamps, are available, they transform a relatively large portion of the power supplied thereto into heat energy so that without a corresponding cooling action overheating of the device is encountered.

Furthermore, from German patent 28 41 112 a light curing device is known which comprises a hood-shaped inner housing that is placed on top of the reflector of the halogen lamp provided therein. In this manner, a substantially dust-tight interior chamber is provided and the inner housing is also provided with cooling ribs.

Despite large surface area cooling ribs at the forward end of the inner housing, too much heat energy is usually observed which results in a great service life reduction or optionally also in failure of the employed constructive components, especially since the cooling air flow is selected such that the edge of the reflector is still cooled but the transition portion between the halogen lamp and the reflector is arranged so as to be relatively protected from the air flow, and cooling by the cooling air flow is thus only minimal.

In order to realize the required cooling action, it is known to provide respectively strong fans. They generate, however, undesirable exhaust air and also cause unpleasant noise. Independent of the exiting direction of the exhaust air generated by the fan, the exiting air flow is disruptive because results in air turbulence within the dental practice which, especially with regard to hygienic considerations, is undesirable.

A further undesirable aspect is that the fan after the curing device has been turned off will continue to run for a while. This necessary in conventional light curing devices in order to avoid heat build-up.

It is therefore an object of the present invention to provide a light curing device of the aforementioned kind which is able to provide over an extended period of time reliably the desired light output but at the same time provides a reduced airflow and is at the same time dimensioned such that heat build-up will be avoided.

SUMMARY OF THE INVENTION

A light curing device for light-induced curing of dental materials in the mouth of a patient according to the present invention is primarily characterized by:

hand-held portion having a housing having a grip;

a light source casing mounted in the housing;

a light source mounted in the light source casing;

a reflector for the light emitted by the light source mounted in the light source casing;

a fan for cooling the light source mounted in the housing;

the light source casing comprising a light source cooling member surrounding the light source and a counter cone member facing the light source;

the light source casing having exterior cooling ribs along the light source cooling member and the counter cone member;

the light source cooling member located adjacent to the reflector and matching the outer contour of the reflector, the cooling ribs provided on the light source cooling member extending parallel to a direction of light emission of the light source and having a forward end and a rearward end.

The light source cooling member is preferably conical.

Advantageously, the cooling ribs of the light source cooling member have a great radial extension in the area of the transition between the reflector and the socket for the light source and the radial extension decreases forward and rearward ends.

Advantageously, the light source casing has a receiving socket for the light source and the light source cooling member extends axially along the receiving socket.

The light curing device further comprises a circuit board mounted in the grip portion, wherein the light source casing has a receiving socket for the light source into which the light source is plugged, wherein the receiving socket is connected directly to the circuit board without cable connection, preferably by soldering.

The circuit board extends through an air flow generated by the fan for cooling the light source and has penetrations for allowing a portion of the air flow to pass through.

Preferably, the entire exterior of the light source casing is provided with cooling ribs, and the cooling ribs have a height decreasing toward the rearward end and the forward end of the light source casing.

The fan in comparison to conventional fans is output-reduced and noise-reduced.

Preferably, the circuit board has laterally adjacent to the receiving socket enlarged metal surfaces, wherein the receiving socket has connecting poles and wherein each one of the receiving sockets has two connecting locations, especially soldering points and wherein the metal surfaces have a size of at least 2 cm$^2$.

Advantageously, the circuit board comprises a voltage and a current sensor positioned in the vicinity of the light source and power electronics for supplying voltage and current to the light source, and the fan are provided in a stationary receiving station of the light curing device.

Preferably, the hand-held portion has a grip extending relative to the optical axis of the reflector at a slant to the rear of the light curing device and the circuit board extends at a slant through the grip at a right angle to the optical axis of the reflector.

The circuit board comprises a power detection device for the light source with which the voltage and the current supplied to the light source are measured, multiplied by one another, and compared to a nominal power. A known portion of the power is branched off for operating the fan and is taken into consideration when determining the actual power of the light source.

The power detection device preferably takes into consideration different cable lengths of a connecting cable connecting the hand-held portion of the light curing device to a stationary receiving station of the light curing device.

The light curing device may further comprise a power control device connected to the power detection device. The power control device includes a cooling period control with which an operating time of the fan for cooling the light source is calculated or set, based on a sum of previous, optionally intermittent, operating periods.

The light curing device may also comprise a heat-absorbing light inlet device for a light guide, especially in the form of an absorption lens. The light inlet device is connected by a heat-transfer connection to the counter cone member.

Advantageously, the light source cooling member and the counter cone member are connected to one another by screwing. The counter cone member preferably has an inner thread.

Advantageously, the fan has a plug-In connector for insertion into the circuit board.

Surprisingly, the inventive solution provides for a dust-tight encapsulation of the entire light-emitting area and at the same time the light source casing can be produced of a metal such as zinc by pressure casting which metals have excellent heat-transfer properties such that the light source casing is externally provided with cooling ribs in order to provide for an intensive cooling. This allows for improved heat dissipation without allowing introduction of dust which would inpede the light output of the light source.

The inventive light source casing extends in the longitudinal direction of the light curing device and surrounds not only a filter lens, which by absorption of infrared radiation is especially hot, but also the area of the fastening or receiving socket for the light source so that due to the good heat conducting connection the dissipation of the convection heat is possible in an especially intensive manner. Since a straight air flow is substantially provided without deflection within the light curing device and the cooling ribs extend in the longitudinal direction and are thus directly exposed to the air flow, an especially intensive cooling can be combined with minimal fan output so that despite the use of a low noise and low output, i.e., minimal air flow, fan an intensive and excellent cooling can be realized.

Surprisingly, this also prevents the risk of a heat build-up even though the interior of the light source casing cannot be reached by the air flow. Due to the reduced flow velocity of the air through the light curing device, the difference between turned-on and turned-off fan, when the light source is switched off, is much reduced, as compared to a relatively strong air flow in conventional light curing devices which will suddenly collapse when the light curing device and thus the fan are switched off.

Inventively, a comparatively large and slowly moving fan is provided which is known in general. Such a fan, which is used in the context of the present invention in a novel application, provides minimal air turbulence and minimal noise pollution in comparison to fans of known light curing devices.

Inventively, the intimate connection of the fastening socket for the light source to the circuit board is especially advantageous. While a person skilled in the art in the past had objections against such intimate connection with respect to the need for protection of sensitive electronic components against intensive heat exposure, the inventive solution provides an especially advantageous embodiment in that the circuit board is provided with large metal surface areas, i.e., in general copper surfaces, in order to aid in heat dissipation. These metal surfaces have a double function in that, on the one hand, they are positioned in the air flow produced by the fan, and, on the other hand, when the fan is turned off, they function as heat radiators. The circuit board comprises passages for the air flow in order to not impede air flow within the light source casing. Such penetrations or openings provide the additional function to impede heat transfer of the fastening socket onto the sensitive electronic components on the circuit board because the heat transfer then takes place via very thin stays.

Surprisingly, such stays, due to their lateral spacing, have the required stability for securing the fastening or receiving socket at the corresponding location while it is understood that the light source casing itself can be supported by respective projections at the housing of the light curing device, respectively, in its interior.

BRIEF DESCRIPTION OF THE DRAWINGS

The object an advantages of the present invention will appear more clearly from the following specification in conjunction with the accompanying drawings, in which.

DESCRIPTION OF PREFERRED EMBODIMENTS

The present invention will now be described in detail with the aid of several specific embodiments utilizing FIGS. 1 through 3.

Figure 1:
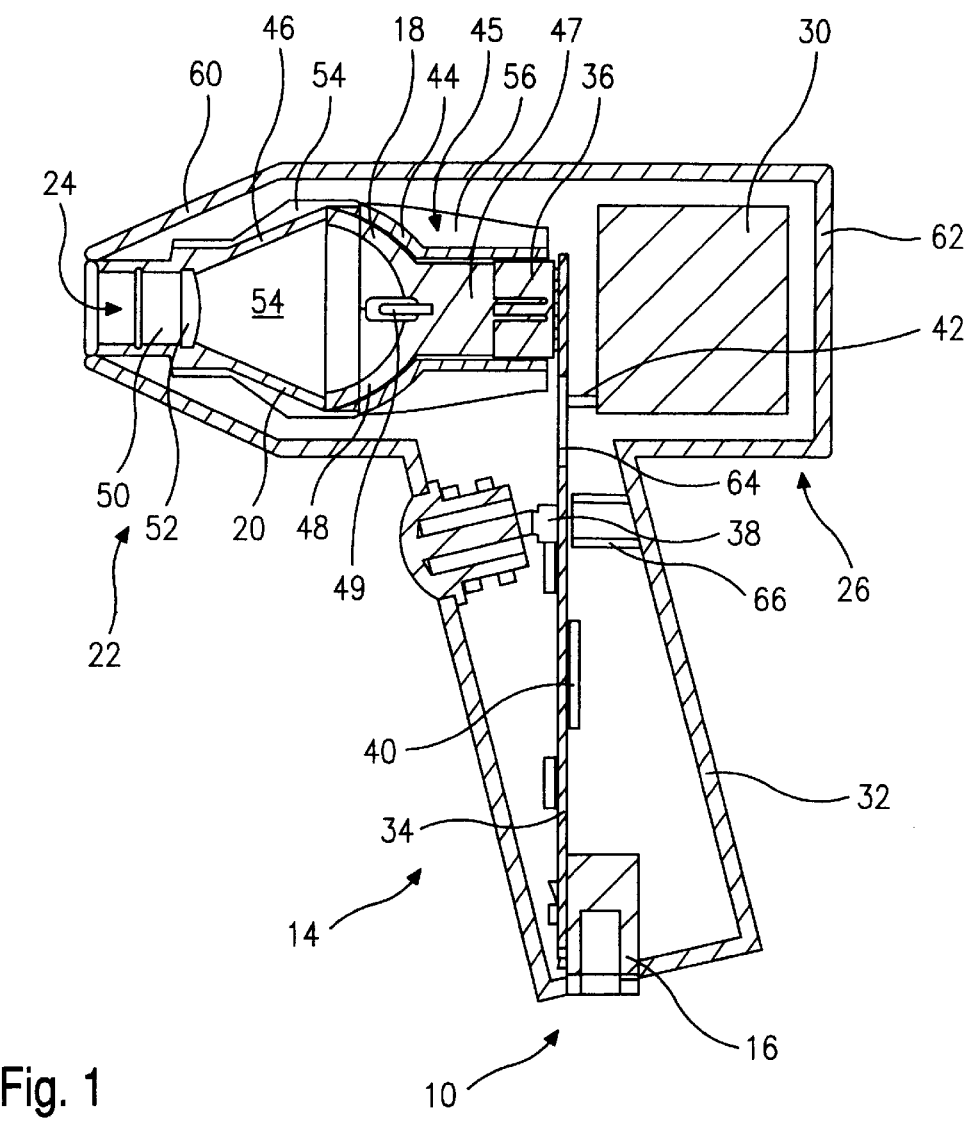
FIG. 1 is an embodiment of the inventive light curing device in a simplified cross-sectional representation.

The hand-held light curing device 10 represented in FIG. 1 has a housing 12 which is substantially pistol-shaped and has a grip portion 14 for holding the light curing device. The grip portion 14 is connected to a non-represented stationary receiving station by a cable connection whereby FIG. 1 shows a plug-in 16 for connecting the cable.

The hand-held portion 14 has a light source 18 which is preferably embodied as a conventional reflector halogen lamp and is received in the light source casing 20. The light source casing 20 has at its forward end 22 a receiving element 24 for a light guiding device such as a light guiding rod which is designed to be introduced into the mouth of the patient. This design is disclosed in German patent application 42 11 235 A1 the disclosure of which is hereby incorporated by reference. At the rearward end 26 of the hand-held portion 14 a fan 30 is supported and a circuit board 34 extends at a slant through the grip 32 of the hand-held portion 14 which provides a fastening or receiving socket 36 for the light source 18, a switch 38 for turning on and off the light curing device, a power detecting electronic 40, and the plug-in 16. In addition, the fan 30 is connected by connectors 42 to the circuit board 34 and in the area of the fastening socket 36 a non-represented temperature sensor is provided. Inventively, the light source casing 20 which encloses the light source 18 is encapsuled so as to be dust-tight within the illuminated area. The light source housing 20 is of a two-part construction and has a rearward portion which is the light source cooling member 44 and a forward portion which is the counter cone member 46. Both parts are coupled mechanically and tightly to one another but are detachable for exchanging the light source. The position of the light source 18 is determined by the light source cooling member 44. The light source cooling member 44 is designed such that it receives the light source 18 in a flush manner so that the screwing action for connection to the counter cone member 46 fixes the position of the light source 18 all directions. In a modified embodiment a temperature-resistant silicone ring is provided which elastically forces the edge of the reflector 48, by action of the counter cone member 46, against the light source cooling member 44. This embodiment is not plagued by tolerance variations.

The inner shape of the light source cooling member 44 is matched as much as possible to that of the light source 18. The transition portion 45 between the reflector 48 and the cylindrical area 47 of the light source, which serves for supporting the incandescent light 49, is critical. The incandescent lamp 49 represents the hottest part of the light curing device and inventively it is suggested to provide large cooling ribs 46 on the light source cooling member 44 as close as possible in the vicinity of the incandescent lamp 49 in order to dissipate the resulting heat with maximum efficiency.

Even though between the outer surface of the reflector 48 and the cylindrical area 46 and the inner surface of the light source cooling member 44 a gap is shown in the drawing, it is understood that an abutment or contact is preferred.

In order to compensate manufacturing tolerances, in a modified embodiment it may be favorable to widen the gap to the forward end of the reflector 48 such that an oversize in this area prevents abutment at the most important transition area 45.

Figure 2:
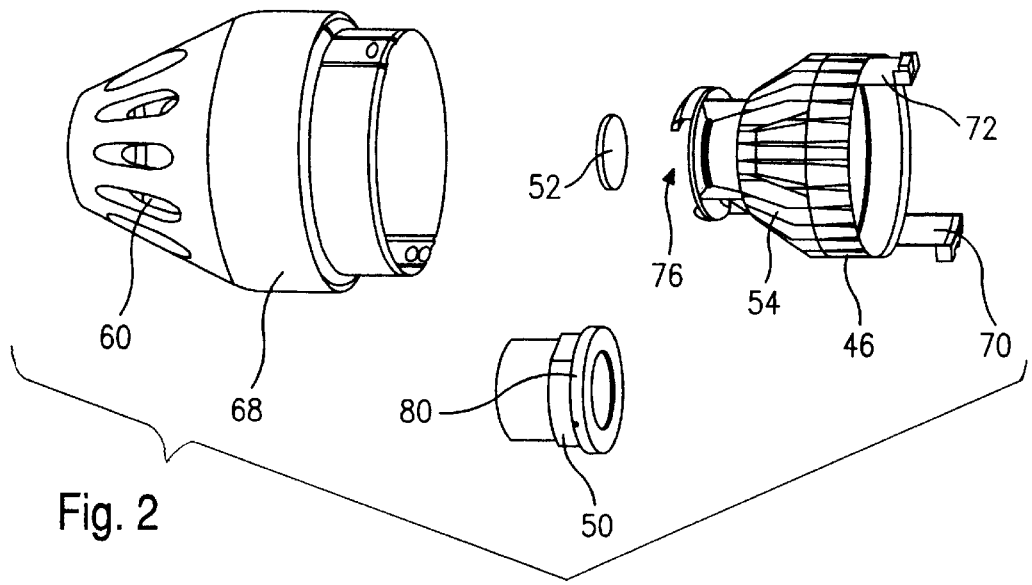
FIG. 2 shows a perspective representation of the forward end of the inventive light curing device in the embodiment according to FIG. 1 showing in particular the counter cone member.

The counter cone member 46 comprises also a receiving member 50 for the light guide, shown especially in FIG. 2, which is covered by a filter lens 52 which is connected to the counter cone member 46 so as to be heat conducting. The filter lens 52 surrounds the interior 54 of the light source casing in a tight manner so that the interior is completely dust-tight even when over many years air flows along the outer surface of the light source casing 44.

Inventively, it is preferred to provide at the counter cone 46 and the light source cooling member 44 cooling ribs 54, 56 which extend substantially over the entire length of the light source casing 20 and which extend parallel to the optical axis of the light curing device but also parallel to the air flow which is produced by the fan 30.

The housing 12 provides at its forward end 22 adjacent of the counter cone member 46 inlet slots 60 and its rearward end 26 air outlet openings 62. The air flow is thus substantially straight and uninhibited through the light curing device so that comparatively minimal air turbulence will result and only a minimal blower output is required to provide the desired cooling action.

Preferably, the light source casing 20 has at its outer side a comparatively rough surface with microscopic depressions which improves the heat transfer relative to the air flowing by. In addition, the circuit board 34 has penetrations or openings 64 which allow air to flow through the circuit board 34, as can be seen in FIG. 3.

The circuit board 34 extends at a slant through the grip 32 but perpendicular to the optical axis of the light emitted by the reflector 48. This allows an inexpensive manufacture and excellent spacial arrangement whereby, preferably, the area of the switch 38 is additionally supported by a supporting device 66.

If needed, an additional small air opening in the area of the plug-in 16 could be provided for cooling the circuit board, i.e., substantially the power detecting electronic 40. This is not required for the aforementioned preferred embodiment with respect to minimal heat loading so that the grip 32 in this embodiment is closed in the downward direction.

As can be seen in FIG. 2, the forward part 68 of the housing 12 of the hand-held device has inlet slots 60. The part 68 is fixedly supported on the counter cone member. For exchanging the lamp, the complete unit of parts 68 and counter cone 46 can be removed by screwing so that the light source 18 with its reflector 48 and its outer edge is freely accessible and can be removed. The counter cone member 46 is provided with flanges 70 and 72 which extend laterally about the light source cooling member 44.

Figure 3:
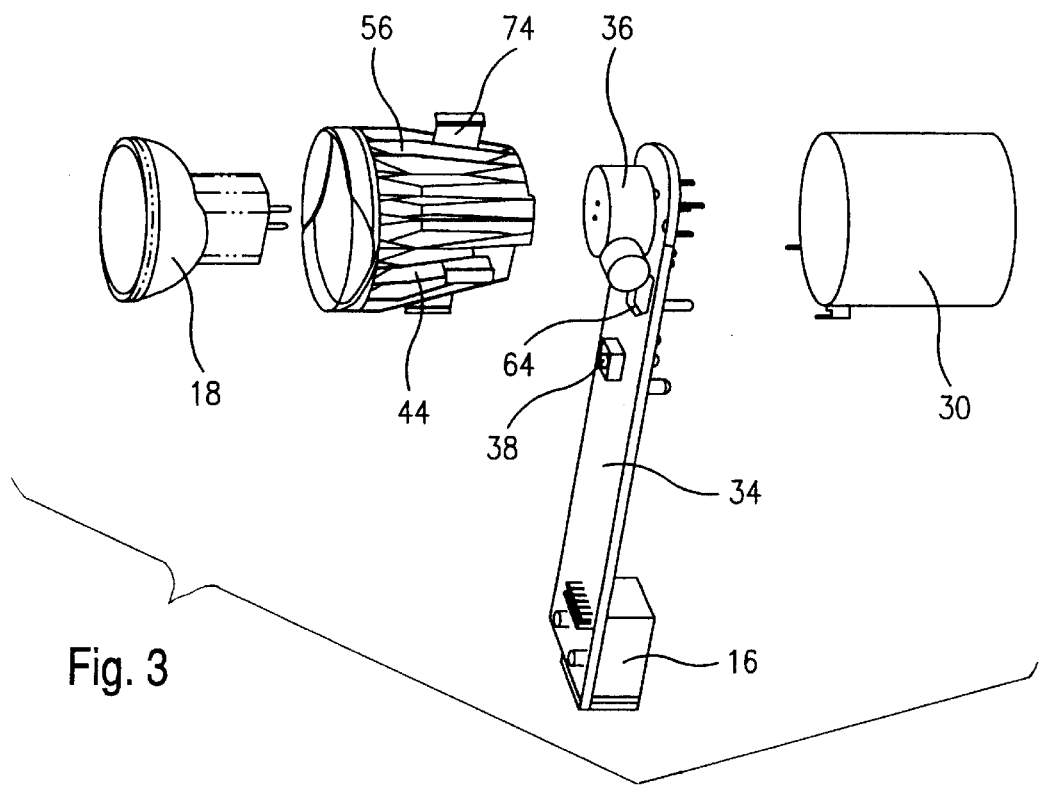
FIG. 3 is a perspective representation of the rearward portion of the inventive light curing device in the embodiment according to FIG. 1, showing especially the cooling member, the light source, the circuit board, and the fan, while the housing of the light curing device is not represented.

In an alternative embodiment it is suggested to screw the counter cone member entirely into the light source cooling member 44 instead of using the screwing action via flanges, whereby optionally additional support devices corresponding to the support devices 74 of FIG. 3 can be provided which ensure proper support of the light source casing 20 within the housing 12.

The counter cone member 46 has a slotted receiving member 76 for the adaptor 50. For mounting, the filter lens 52 Is inserted with tight fit into a corresponding recess and the adaptor 50 with projection edge 80 is then inserted from the side. Between the adaptor 50 and the counter cone member 46 an O-ring is provided which secures and protects the lens and provides accordingly already a tight seal of the forward end of the counter cone member 46.

As can be seen in FIG. 3, not only the counter cone member 46 but also the light source cooling member 44 comprises numerous circumferential uniformly distributed cooling ribs 56. The cooling ribs extend over the area of the fastening socket 36, which is received in the circuit board 34.

FIG. 3 also shows the through opening 64 for allowing passage of cooling air through the circuit board 34. A corresponding through opening is provided at the other side of the circuit board which is covered by the fastening socket, and the cooling air can thus pass without hindrance through the inlet slots 60, the cooling ribs 54 the cooling ribs 56, and the fan 30.

The present invention is, of course, in no way restricted to the specific disclosure of the specification and drawings, but also encompasses any modifications within the scope of the appended claims.

We claim:

1. A light curing device for light-induced curing of dental materials in the mouth of a patient, said light curing device comprising:

a hand-held portion having a housing having a grip;

a light source casing mounted in said housing;

a light source mounted in said light source casing;

a reflector for the light emitted by said light source mounted in said light source casing;

a fan for cooling said light source mounted in said housing;

said light source casing comprising a light source cooling member surrounding said light source and a counter cone member facing said light source;

said light source casing having exterior cooling ribs along said light source cooling member and said counter cone member;

said light source cooling member located adjacent to said reflector and matching an outer contour of said reflector, wherein said cooling ribs provided on said light source cooling member extend parallel to a direction of light emission of said light source and have a forward end and a rearward end.

2. A light curing device according to claim 1, wherein said light source cooling member is conical.

3. A light curing device according to claim 1, wherein said cooling ribs of said light source cooling member have a greatest radial extension in an area of transition between said reflector and a receiving socket for said light source and wherein the radial extension decreases toward said forward and rearward ends.

4. A light curing device according to claim 1, wherein said light source casing has a receiving socket for said light source and wherein said light source cooling member extends axially along said receiving socket.

5. A light curing device according to claim 1, further comprising a circuit board mounted in said grip portion, wherein said light source casing has a receiving socket for said light source into which said light source is plugged, wherein said receiving socket is connected directly to said circuit board without cable connection, preferably by soldering.

6. A light curing device according to claim 5, wherein said circuit board extends through an air flow generated by said fan for cooling said light source and has penetrations for allowing a portion of the air flow to pass through.

7. A light curing device according to claim 5, wherein said circuit board has laterally adjacent to said receiving socket enlarged metal surfaces, wherein said receiving socket has connecting poles and wherein each one of said receiving sockets has two connecting locations, especially soldering points, and wherein said metal surfaces have a size of at least 2 $cm^2$.

8. A light curing device according to claim 5, wherein said circuit board comprises a voltage and current sensor positioned in the vicinity of said light source and wherein power electronics for supplying voltage and current to said light source and said fan are provided in a stationary receiving station of said light curing device.

9. A light curing device according to claim 5, wherein said grip of said hand-held portion extends relative to an optical axis of said reflector at a slant to the rear of said light curing device and wherein said circuit board extends at a slant through said grip at a right angle to said optical axis of said reflector.

10. A light curing device according to claim 9, wherein said circuit board comprises an power detection device for said light source with which the voltage and the current supplied to said light source are measured, multiplied by one another, and compared to a nominal power, wherein a known portion of the power is branched off for operating said fan and is taken into consideration when determining the actual power of said light source.

11. A light curing device according to claim 10, wherein said power detection device takes into consideration different cable lengths of a connecting cable connecting said hand-held portion of said light curing device to a stationary receiving station of said light curing device.

12. A light curing device according to claim 10, further comprising a power control device connected to said power detection device, wherein said power control device includes a cooling period control with which an operating time of said fan for cooling said light source is calculated or set based on a sum of previous, optionally intermittent, operating periods.

13. A light curing device according to claim 5, wherein said fan has a plug-in connector for insertion into said circuit board.

14. A light curing device according to claim 1, wherein the entire exterior of said light source casing is provided with said cooling ribs and wherein said cooling ribs have a height decreasing toward a rearward end and a forward end of said light source casing.

15. A light curing device according to claim 1, wherein said fan in comparison to conventional fans is output-reduced and noise-reduced.

16. A light curing device according to claim 1, further comprising a heat-absorbing light inlet device for a light guide especially in the form of an absorption lens, said light inlet device connected in a heat-transfer connection to said counter cone member.

17. A light curing device according to claim 1, wherein said light source cooling member and said counter cone member are connected to one another by screwing.

18. A light curing device according to claim 17, wherein said counter cone member has an inner thread.

\* \* \* \* \*